(12) United States Patent
Baarman

(10) Patent No.: US 12,186,441 B2
(45) Date of Patent: Jan. 7, 2025

(54) DISINFECTION AND MONITORING OF A BODY CONTACT DEVICE

(71) Applicant: UV Partners, Inc., Grand Haven, MI (US)

(72) Inventor: David W Baarman, Fennville, MI (US)

(73) Assignee: UV Partners, Inc., Grand Haven, MI (US)

( * ) Notice: Subject to any disclaimer, the term of this patent is extended or adjusted under 35 U.S.C. 154(b) by 365 days.

(21) Appl. No.: 17/771,281

(22) PCT Filed: Oct. 5, 2020

(86) PCT No.: PCT/US2020/054199
§ 371 (c)(1),
(2) Date: Apr. 22, 2022

(87) PCT Pub. No.: WO2021/080763
PCT Pub. Date: Apr. 29, 2021

(65) Prior Publication Data
US 2022/0387643 A1  Dec. 8, 2022

Related U.S. Application Data

(60) Provisional application No. 62/924,327, filed on Oct. 22, 2019.

(51) Int. Cl.
*A61L 2/10* (2006.01)
(52) U.S. Cl.
CPC ............. *A61L 2/10* (2013.01); *A61L 2202/11* (2013.01); *A61L 2202/14* (2013.01); *A61L 2202/24* (2013.01)

(58) Field of Classification Search
CPC .... A61L 2/10; A61L 2202/11; A61L 2202/14; A61L 2202/24
(Continued)

(56) References Cited

U.S. PATENT DOCUMENTS

| 11,213,695 B2 | 1/2022 | Fewkes et al. |
| 2009/0257910 A1 | 10/2009 | Segal |

(Continued)

FOREIGN PATENT DOCUMENTS

| CN | 1487842 A | 4/2004 |
| JP | 2009-261957 | 11/2009 |

(Continued)

OTHER PUBLICATIONS

International Search Report and the Written Opinion of the International Searching Authority for International Application No. PCT/US2020/054199, mailed Feb. 11, 2021.

(Continued)

*Primary Examiner* — Nicole M Ippolito
(74) *Attorney, Agent, or Firm* — Warner Norcross + Judd LLP

(57) ABSTRACT

A disinfection system that provides homogenous UV light output. The system can utilize a sensor system to detect proper use provide user feedback on safety and functional operation. By tracking cumulative dosage of low energy UV-C the system can disinfect without violating safety exposure standards. The system can automatically provide a disinfection dose according to the type and length of body contact device the disinfection device is mounted to, while tracking operational details. The system can include crypto security that enables a safer ecosystem and HIPAA compliant statistic sharing of operational parameters.

26 Claims, 10 Drawing Sheets

(58) Field of Classification Search
USPC .................... 250/453.11, 454.11, 455.11
See application file for complete search history.

(56) References Cited

U.S. PATENT DOCUMENTS

| | | |
|---|---|---|
| 2015/0231287 A1 | 8/2015 | Lin et al. |
| 2016/0310711 A1 | 10/2016 | Luxon et al. |
| 2017/0296686 A1 | 10/2017 | Cole |
| 2018/0200396 A1* | 7/2018 | Messina .................. A61L 2/10 |
| 2019/0008607 A1 | 1/2019 | Bauco et al. |
| 2019/0192814 A1 | 6/2019 | Tang et al. |

FOREIGN PATENT DOCUMENTS

| | | |
|---|---|---|
| JP | 2015-528709 | 10/2015 |
| JP | 2016-518872 | 6/2016 |
| JP | 2017-512603 | 5/2017 |
| JP | 2017-526402 | 9/2017 |
| JP | 2019-076624 | 5/2019 |
| WO | 2013/181393 | 12/2013 |
| WO | 2014/159855 | 10/2014 |
| WO | 2015/105916 | 7/2015 |
| WO | 2016/001776 | 1/2016 |
| WO | 2019/190967 | 10/2019 |

OTHER PUBLICATIONS

Kirk, A.M. et al., A Medical Therapeutic Devices—Application and Design, 1st edition, May 31, 1988, Shanghai Science and Technology Literature Publishing House, pp. 159-160.

Xinghua, Zhang, A Water-Based Coatings-Raw Material Selection-Formulation Design-Production Process, 1st ed. Jan. 31, 2020, China Light Industry Publishing House, p. 62.

* cited by examiner

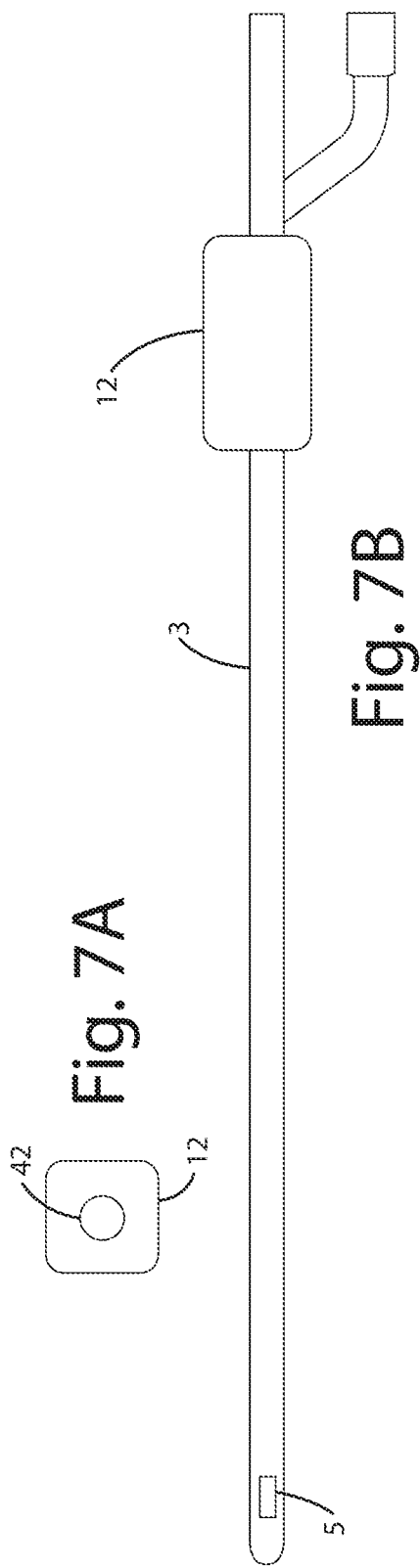
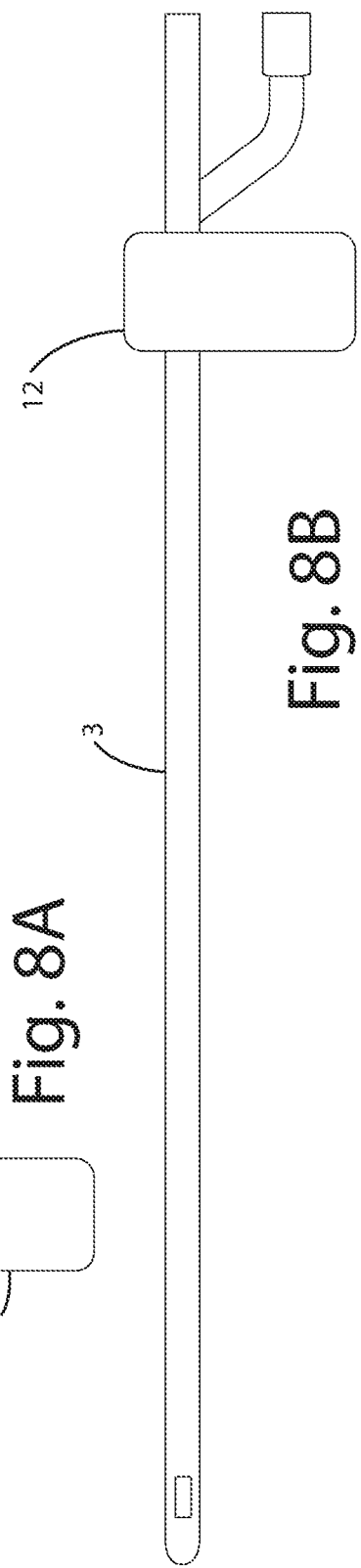

DISINFECTION AND MONITORING OF A BODY CONTACT DEVICE

BACKGROUND OF THE INVENTION

The present invention relates to various ways to reduce or eliminate infections caused by devices contacting human body parts.

There are a variety of different devices that contact the human body and can potentially cause infection. For example, a catheter is a thin tube, often made of soft plastic material, that can be inserted into the body. There are a variety of different catheters, such as urinary catheters to drain urine and peripheral venous catheters for intravenous therapy.

One commonality among catheters is that germs, for example bacteria or yeasts, can spread via the catheter and cause infection at or near the point of body contact. For example, urinary catheters, can cause catheter-associated urinary tract infections (or "CA-UTI"). Germs can enter the urinary tract when the catheter is being inserted or while it remains in the bladder.

Catheters can be indwelling or intermittent. FIG. 1 illustrates a prior art embodiment of an indwelling catheter, often referred to as a "Foley" catheter. The catheter includes a balloon port 1, a urinary drainage port 2, a catheter shaft 3, a balloon 4, and an opening or eyelet 5. The balloon 4 can be inflated via the balloon port 1 in order to keep the catheter in the bladder. The eyelet 5 can drain urine through the catheter shaft 3 to the drainage port 2, which can be connected to a drainage tube and collection bag.

Known practices to reduce catheter-associated infections include limiting the amount of time the catheter is in place, utilizing sterile techniques by trained professionals for catheter installation, cleaning the area where the catheter will be inserted before insertion. However, even adhering to best practices for hygienic catheter installation and maintenance, catheter-associated infections can and still do occur.

Some attempts to reduce catheter-associated infections have been made by applying an antimicrobial coating to the catheter surface. The antimicrobial coating can have antifouling or biocidal properties, or both. Antifouling coatings do not kill the microbes directly, but instead prevent the attachment of bacteria on the surfaces that allow the formation of biofilms. Biocidal catheter materials are designed to kill the microbes instead of minimizing their deposition. In practice, the materials of the antimicrobial coating leach out their antimicrobial agent and do not let the microbe come in contact with the catheter. While this can aid in preventing encrustation and biofilm formation, these antimicrobial coating solutions have largely been rejected due to health concerns for the patient and other potential side effects.

Some attempts have also been made to instantaneously dose medical devices, such as catheters, with high dosages of ultraviolet light (UV) for disinfection. Some known solutions require placement of the medical device into a sealed sterilization chamber that is flooded with UV light. While this may be effective in disinfecting the device, placing the entire body contact device within a sterilization chamber is cumbersome and time consuming. Further, the UV light cannot be administered while the device is installed in the patient. And, the medical device must be removed from the chamber in order to be used on the patient potentially re-exposing the device to bacteria before use. Other UV light solutions that don't utilize a sterilization chamber have largely been rejected because of concerns related to potential damage of patient skin or tissue from the UV light.

SUMMARY OF THE INVENTION

The aforementioned challenges are overcome by the apparatuses, systems, and methods of the present invention. The embodiments of this invention provide a practical solution in the applications of disinfecting a body contact device with simplicity and effectiveness. The invention provides solutions to past problems that have been observed related to infection with body contact devices. Specifically, the proposed embodiments provide a disinfection device configured to interface, join, or attach to a body contact device. The disinfection device is configured to shine UV light from a UV source toward the body contact device to disinfect the body contact device.

Appropriate UV dosing can be provided along the body contact device. The body contact device can include UV transmissive materials that assist in distribution of the UV light and appropriate UV dosing for disinfection of the body contact device. In one embodiment, uniform UV dosing is provided along a portion of or substantially all of the outer perimeter or surface of the body contact device.

A UV blocking pattern can be provided between the UV source and body contact device, for example along a portion of the surface of the body contact device, to mask higher intensity areas of UV light and effectively reflect that energy. The blocking pattern can have a gradient to assist in providing uniform or appropriate UV light dosing along the length of the body contact device. The intensity of the UV source can be configured such that the UV illumination along a length of the body contact device, including toward the proximal end, is sufficient for disinfection.

The disinfection device can control the UV source based on a variety of factors. For example, the disinfection device can configure the UV intensity based on information from or characteristics of the particular body contact device to which it interfaces. In one embodiment, the disinfection device includes an RFID reader, or other communication system, that communicates with an RFID tag, or other communication system, associated with the body contact device. The communication system may include a transceiver for communication with a remote server instead of or in addition to communication with the communication system associated with the body contact device. The length and/or type of material of the of the body contact device can be utilized to determine the UV intensity that will provide effective and appropriate disinfection while meeting safety standards and/or protocols.

The disinfection device can monitor and control the UV source based on the cumulative UV dose over time. The disinfection device can provide low UV dosage over time such that the UV dosage is sufficient for disinfection without exceeding a predetermined intensity threshold associated with known safety protocols or standards. For example, the disinfection device can monitor and control the UV source to ensure the cumulative UV dose provided to the body contact device is maintained under a permissible level over a certain time period.

The disinfection device can be joined, attached, or mounted to the body contact device, for example via integral attachment features or an overwrap. Integral attachment features on the body contact device and disinfection device can cooperate to consistently mount the disinfection device at the same position on the body contact device, which enables a fixed starting point or datum from which the length of the body contact device or other characteristics can be referenced. Where an overwrap is utilized, it can secure the disinfection device and the body contact device to each other, and also may secure the disinfection device, and body contact device to a body surface, for example where a patient has a wound, port, IV, tube entry, needle entry, drain, etc.

In some embodiments, the body contact device is a catheter or other medical device that includes tubing. The body contact device may be outfit with a light transmission system. In one embodiment, the light transmission system includes one or more light guides positioned along the tubing of the body contact device. The light guide assists in providing UV light from the UV source evenly and efficiently over the length of the tubing of the body contact device. In another embodiment, the light transmission system includes one or more light pipes positioned along UV transmissive tubing of a body contact device. The light pipe can provide a rejuvenated UV source toward the proximal end of the body contact device. A UV reflecting, absorbing, or blocking pattern can be provided at the light pipe termination point to mask higher intensity UV light near the light pipe termination point and effectively reflect that energy back into the body contact device. In some body contact devices, the light transmission system may include a combination of light guides and light pipes.

In some embodiments, the body contact device is a wound/dressing device for covering or dressing a patient's wound or another medical device that is secured against an area of a patient's body surface susceptible to infection. The body contact device may include a UV transmissive fluid absorbent material along with an overwrap for securing the UV transmissive fluid absorbent material to a wound area of a body surface or dressing a wound. The disinfection device may be a UV Internet of Things ("IOT") wound device. An overwrap for securing the UV transmissive fluid absorbent material can be utilized to secure the UV IOT wound device to the fluid absorbent material and also can be utilized to secure the combination to a wound area of a body surface. The UV IOT wound disinfection device outputs a UV light pattern toward the UV transmissive fluid absorbent material for disinfecting the body contact device. The UV IOT device can include a sensor system with one or more sensors that can sense various characteristics relating to the body contact device, such as a moisture sensor for sensing a moisture level of the fluid absorbent material and any associated leakages and a temperature sensor for sensing a temperature of the fluid absorbent material. The UV IOT device can also disinfect and track various states of the body contact device such as those related to dressing conditions, movement, temperature, capacitance, moisture, and any other states or state changes associated with the body contact device.

The disinfection device can include a housing, a UV source, a UV driver, a sensor system, and a controller. The disinfection device may include a battery that powers the various electronics in the disinfection device. The housing can be attachable to the body contact device, for example via an overwrap or a snap-fit or other integral attachment feature. The disinfection device may also include a UV reflector for directing UV-C illumination toward the proximal end of the body contact device. The disinfection device may also include a sensor system with one or more sensors. Further, the disinfection device may include an RFID reader that can communicate with an RFID tag embedded or otherwise attached to the body contact device. The RFID can enable tracking life, use, manufacturing date, and type of body contact device. The RFID tag can include information that the controller can use for controlling the UV-source. For example, the RFID tag may include a UV-C intensity setting or appropriate characteristics of the body contact device that the controller can utilize to calculate one or more appropriate control settings.

The disinfection system can provide low dosage UV-C light over time to eliminate pathogens while meeting safety exposure requirements. In addition, the disinfection system can provides homogenous light output and tracks patient movement, drainage, temperatures, times and other valuable data that can be used to assist diagnosis and track other potential problems. Embodiments of the present invention effectively turn a catheter, wound treatment, or other body contact device into a smart device with disinfection and tracking capabilities.

BRIEF DESCRIPTION OF THE DRAWINGS

FIGS. 7A and 7B illustrates a sectional view and top view of one embodiment of an inline UV-C attachment device.

FIGS. 8A and 8B illustrates a sectional view and top view of one embodiment of a side profile UV-C attachment device.

DESCRIPTION OF CURRENT EMBODIMENT

Figure 1:
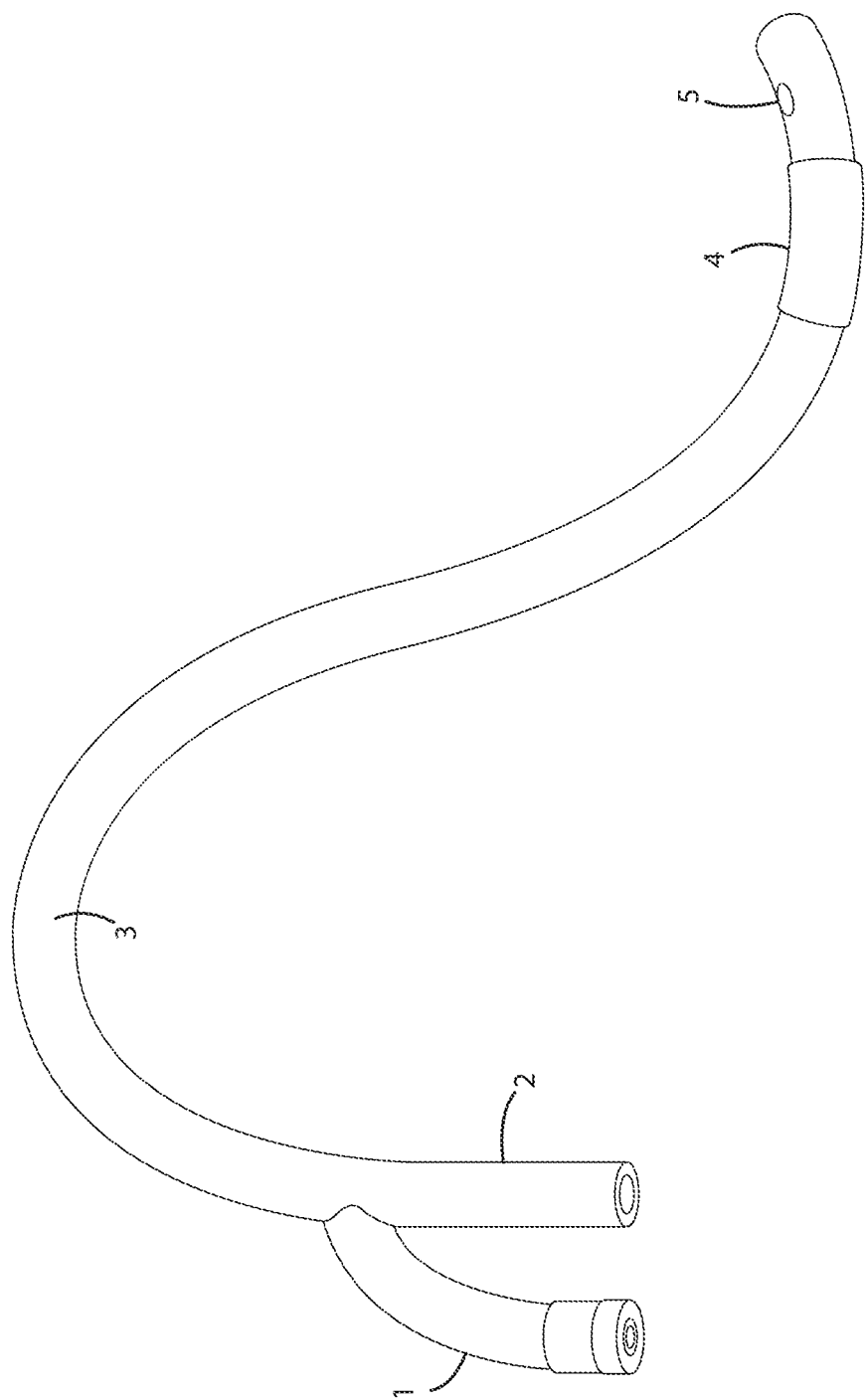
FIG. 1 illustrates a prior art embodiment of a Foley catheter.
Figure 2:
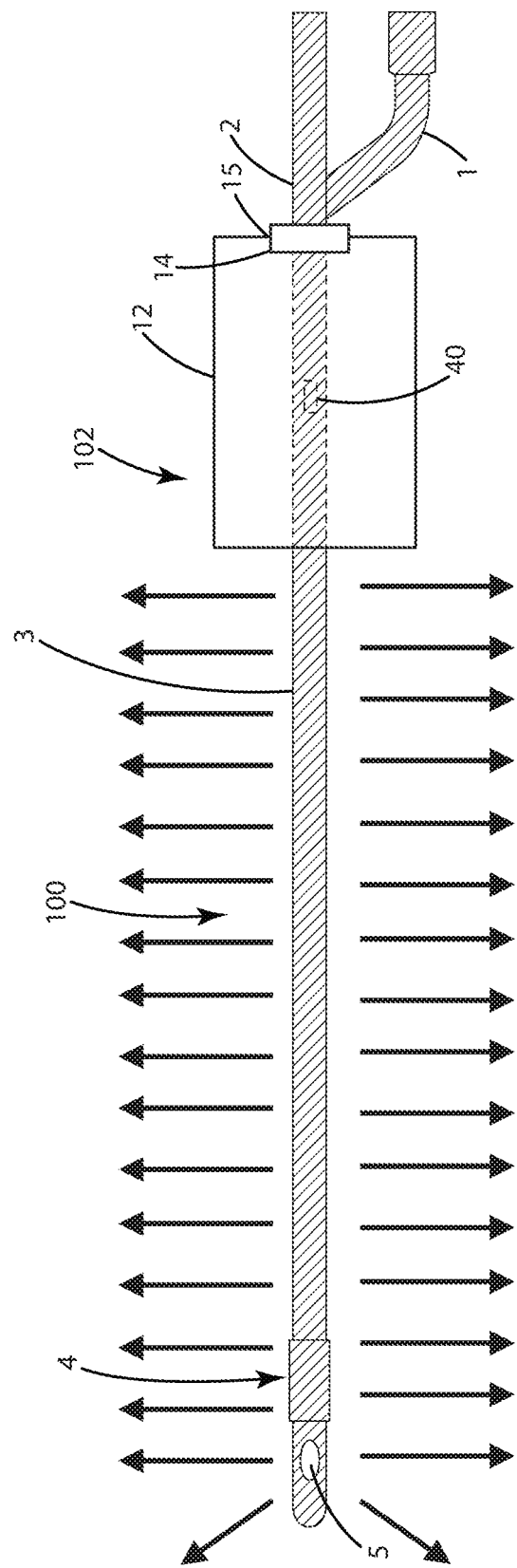
FIG. 2 illustrates a plan view of one embodiment of a UV-C disinfection system of the present invention.
Figure 3:
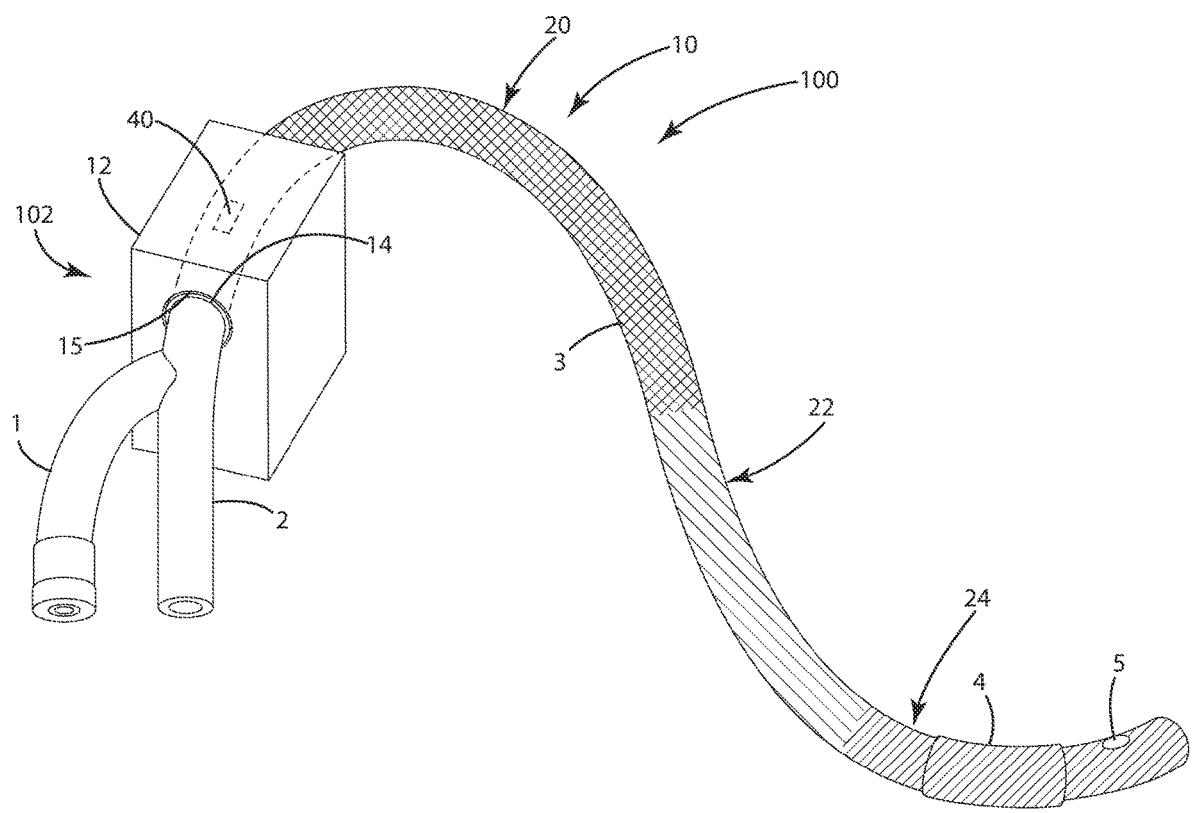
FIG. 3 illustrates a perspective view of one embodiment of a UV-C disinfection system of the present invention.

The present invention generally relates to apparatuses, systems, and methods for use in UV disinfection of a body contact device, such as a catheter or dressing. FIGS. 2 and 3 illustrate one embodiment of a disinfection system including a body contact device 100 and disinfection device 102.

For ease of explanation and to assist in providing clarity, the body contact device illustrated in FIGS. 2-8B and discussed in large part relates to a Foley urinary catheter. However, a person of ordinary skill in the art will appreciate that the various features and aspects of the invention are applicable to other body contact devices such as IV catheters, other type of urinary catheters, general wound disinfecting devices for tubes, ports (dialysis etc.) IV's, incisions, chest tubes, and essentially any other body contact device capable of spreading or causing infection.

Perhaps as best shown in FIG. 3, with the exception of the integral attachment features 14, the UV blocking pattern 10 (20, 22, 24), and the RFID tag 40, the catheter 100 is a standard Foley catheter that includes a balloon port 1, a urinary drainage port 2, a catheter shaft 3, a balloon 4, and an opening or eyelet 5. The balloon 4 can be inflated via the balloon port 1 in order to keep the catheter in the bladder. The eyelet 5 can drain urine through the catheter shaft 3 to the drainage port 2, which can be connected to a drainage tube and collection bag. The drainage tube connected to the drainage port is typically made of polyvinyl chloride, which is not UV transmissive and therefore prevents the transmission of UV light.

A catheter shaft or tube 3 is typically a flexible tube or elongated hollow structure made of latex, silicone, Teflon, or thermoplastic material that can be inserted into the body creating a channel for the passage of fluid or the entry of a medical device. The tubing 3 is a UV transmissive material such that when a disinfection device is attached toward the distal end of the catheter tubing and transmits UV illumination toward the proximal end, the UV light transmits along and through the tubing to the external surface. If a sufficient intensity of UV light reaches the surface, the UV light will disinfect the surface by destroying any pathogens residing there. However, if too much UV light reaches the external surface that comes into contact with the human body, it can create issues. One of the goals of the present invention is to provide, consistently along the length of the catheter surface, a UV light dosage sufficiently large to disinfect the surface but not so large so as to over dose the surface.

The intensity of the disinfection at the surface of the catheter is a product of the length of the catheter. The longer the catheter, the more intensity required at the source so that by the time the UV energy reaches the end of the catheter the intensity is a sufficient dosage. However, the high intensity near the source can create issues. This can be countered with an external pattern printed on the catheter. The halftone pattern is set to the allowable percentage of intensity to homogenize the UV-C energy over the length of the tube, which is made of UVC transmissive material. Providing homogenized light output prevents over dosing at the catheter surface.

FIG. 3 illustrates a representation of the printed pattern of energy reduction. As referenced in FIG. 9 the inverse square law, discussed in more detail herein, causes the UV intensity to fall off over the length of the catheter. FIG. 3 also shows the RFID tag 40 and the snap detail 14 for mounting/locating the disinfection device.

In some embodiments, the integral attachment feature 14A of the catheter 100 pairs with an integral attachment feature 15A on the housing 12 of the disinfection device 102 to removably join or mount the disinfection device 102 to the catheter 100. The integral attachment features cooperate to consistently position and fix the disinfection device 102 in place relative to the catheter 100. In one embodiment, the integral attachment features 14A, 15B can provide a snap-fit that provides proper placement of the disinfection device with respect to the catheter. In the depicted embodiment, the housing 12 of the disinfection device 102 includes an aperture 12 that leads to passage-way 42. The annular aperture includes a bulge 15A and the catheter tube 3 includes an integral or separate collar 14 that includes a groove or ditch 14A. To install the disinfection device 102 on the catheter 100, the proximal end of the catheter tube 3 can be fed through opening 15 and through passage-way 42 in the housing 12 of the disinfection device 102. The tubing 3 can be routed through the disinfection device until the integral attachment feature 14A of the collar 14 snap-fits in place with the integral attachment feature 15A located on the annual aperture 15 of the housing. Although in the depicted embodiment, one of the integral attachment features 14A is a channel on a collar of the catheter tubing 3 and another of the integral attachment features 15A is a ridge or bulge located within the annual aperture 15 of the housing 12, other configurations can be implemented. For example, the bulge and channel can be reversed, the aperture 15 and collar 14 may be a shape other than annular. In the current embodiment, the collar 14 can be a swelled portion of the same material that the tubing 3 is made from. Alternatively, the collar 14 can be made from a different material, such as a stiffer material that facilitates the snap-fit. In another alternative embodiment, the collar 14 can be a separate component that is joined with the tubing, for example by way of adhesive or friction fit. The disinfection device 12 may optically include a wall 15B to assist in installation. For example, the wall can prevent the collar 14 from sliding past the integral attachment feature 15A. Although the present figures depict a single set of integral attachment features, in alternative embodiments, two separate sets of integral attachment features can be provided. For example, multiple sets of integral attachment features can be provided on the collar 14 and aperture 15 to create a more secure connection. Alternatively, or in addition, two or more sets of integral attachment features could be provided, one at each end of the passage-way 42.

In another alternative embodiment, an integral attachment feature on the disinfection device can be configured to catch catheter tubing 3 within the passage-way 42. The catheter tubing may include a marking or physical notch to indicate desired placement of the disinfection device.

The disinfection device can be consistently positioned/mounted near the drainage port and balloon port junction. The pre-determined relative placement, enables the control system of the disinfection device to configure the UV-C source to provide an appropriate amount of UV-C intensity that can travel and disinfect the length of the UV-transmissive catheter shaft 3 reaching all the way to the proximal end near opening 5. In other words, the connection point provides a dose delivery datum so that the UV-C intensity can be set within a range that ensures the UV-C intensity is both high enough to reach the proximal end of the catheter shaft 3 before dissipating to levels too low for effective disinfection, and also low enough to ensure there is not too much excess UV-C radiation. For example, in some embodiments, the disinfection device is configured to energize the UV-C source such that it has an initial intensity of about 60 microwatts. For a 18 cm length catheter, about 2.97 microwatts of UV-C energy will reach the proximal end of the catheter shaft 3. The precise values can vary, for example depending on the UV-transmissive materials, precise shape/configuration of the catheter tubing, or other characteristics of the catheter 100.

The UV blocking pattern 10 reflects the UV-C energy along the length of the UV transmissive tubing 3 of the body contact device. In some embodiments, the blocking pattern 10 scales with a gradient from the distal end to the proximal end. That is, the blocking pattern may scale how much UV-C energy is blocked from a high amount toward the distal end of the catheter near the UV-source where the intensity is higher to blocking a low amount toward the proximal end of the catheter far from the UV-source where the intensity is lower. For simplicity, FIG. 3 illustrates three zones of UV blocking pattern 10. The first zone 20 blocks the most UV-C light, the second zone 22 blocks less, and the third zone 24 blocks the least UV-C light. The zones help to illustrate that the amount of UV light blocked by the pattern decreases as the light travels along the UV transmissive tubing 3 from the UV source in the disinfection device toward the proximal end of the catheter. The UV blocking pattern 10 can provide a sectioned gradient as depicted in FIG. 3, or a more gradual gradient that changes over the length of the UV transmissive tubing 3. For example, the gradient of the blocking pattern 10 can be modeled after the blocking pattern percentages depicted in the FIG. 9 graph where the blocking pattern 10 blocks almost 98% of the UV-C intensity at 1 cm from the UV-C source and 0% at 18 cm from the UV-C source.

The UV blocking pattern 10 can reflect UV light back in to the catheter. The amount of reflection of the blocking pattern provides at a particular position on the catheter tube depends on a number of factors, perhaps most notably the density of the mesh of the pattern as well as the material content of the pattern. The characteristics of the pattern can be adjusted in order to counteract the losses due to the UV light dissipating as it travels along the UV transmissive material. That is the UV blocking pattern can vary along the length of the tubing to reflect a percentage of UV light such that the desired dosage level passes through the UV blocking pattern. In this way a consistent and uniform dosage level can be provided along the entire length of the catheter tubing.

Figure 9:
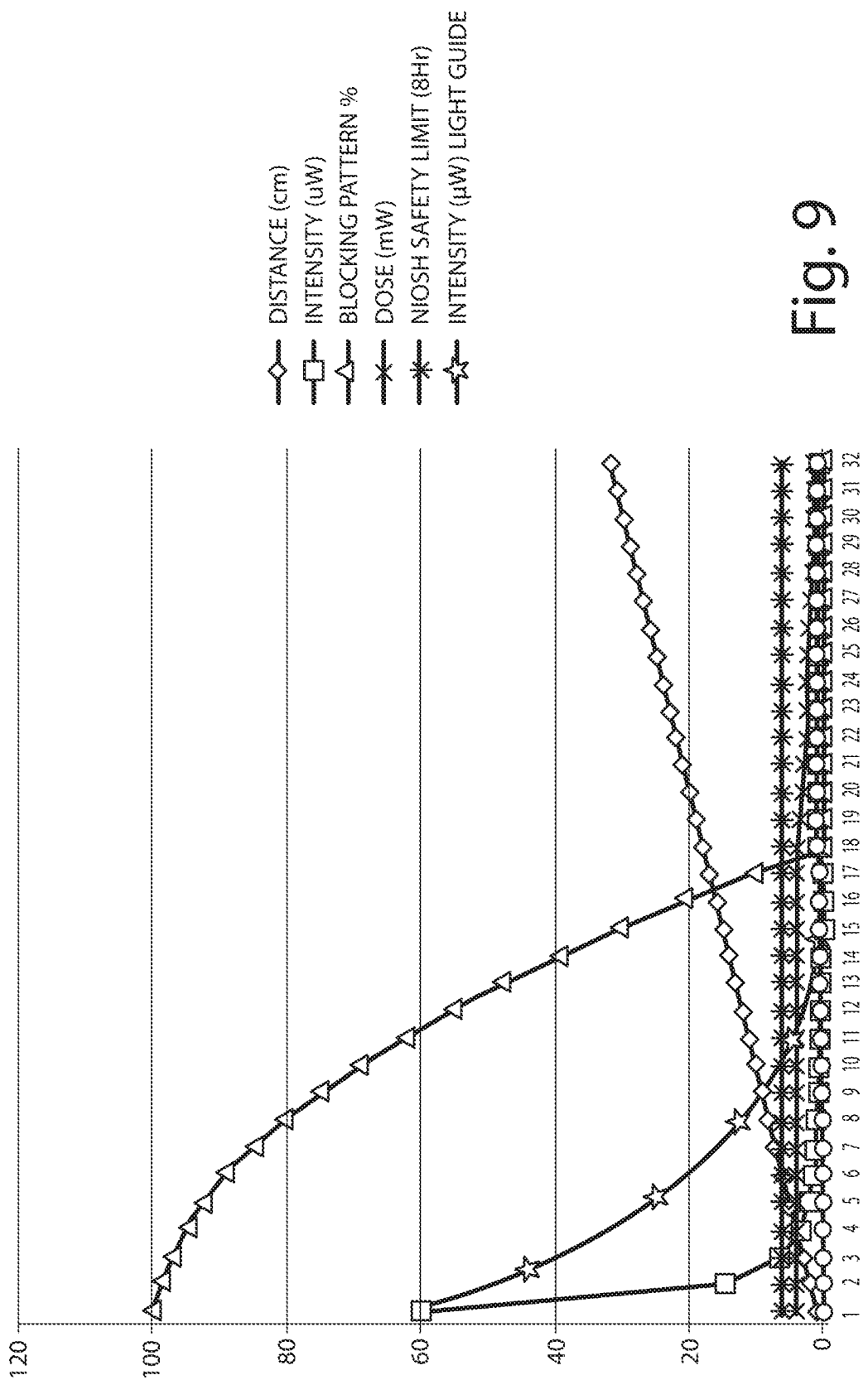
FIG. 9 illustrates a graph showing UV-C dosages and blocking pattern percentages with one embodiment of the present invention over various lengths of body contact devices.

The inverse square law assures the starting intensity at the UV source is much greater that the finished intensity near the end of the catheter. For example, UV light intensity dissipates as it travels away from the source as depicted in FIG. 9 by the 60 microwatt intensity dropping to near 3 microwatts at about 18 cm. Accordingly, by calculating the inverse square law for the given intensity and desired UV dosage, the characteristics of the blocking pattern can be defined. For example, the density of the mesh pattern and/or content of the blocking pattern can be configured to mask the higher intensity areas and effectively reflect that energy back into the tubing. This provides a high end baseline for the exposure to be encountered.

The specific intensity values at particular distances conform to the inverse square law, but the observed intensities along the length of the UV transmissive tubing in practice may be more complex due to a variety of reasons. For example, the UV transmissive tubing to some extent can act as a light guide that prevents dilution of energy while propagating the UV light. Accordingly, the characteristics of the blocking pattern can also be determined experimentally by measuring the intensity values at several points along the UV transmissive tubing or by calculation factoring in the effects of the UV transmissive materials. The characteristics of the blocking pattern can be defined based on the calculated and/or experimental values to produce a homogenized light output that prevents over dosing the surface of the catheter.

The UV blocking pattern 10 can be printed directly on to the catheter shaft 3. The blocking pattern 10 can be composed of a UV-C semitransparent 80-90% blockage white silicone based material with TiO2 for reflection back into the catheter tube 3. In order to allow the printing material to adhere to the tubing, printing can be performed on the hot post extruded material while in process. In addition, the mesh pattern can be imprinted by coextruding a mesh of another material that does not pass UVC or is substantially opaque to UVC. This process co-bonds the materials during the extrusion process for a smooth finish. If desired, a thin sheath can be added that makes the outer layer smooth for insertion. That is, the pattern can be applied along the length of the body contact device such that the amount of UV light reflected back into the body contact device, absorbed, or otherwise blocked by the pattern is greatest toward the distal end close to the UV source where the UV light intensity is greatest and the amount of UV light reflected, absorbed, or blocked can decrease with the gradient toward the proximal end of the body contact device where the intensity of the UV light is lower due to the dispersion of the UV light.

Essentially any material that can block, absorb, or reflect UV light can be utilized to print the blocking pattern. The reflection characteristics of the material can be selected depending on the application and how much UV light reflection is desired. Further, different materials can be utilized with adjustments to the structure of the blocking pattern being used to alter the overall reflective characteristics. Further, the UV blocking pattern material can be selected to reflect UV-C light between 200 nm-280 nm. The structure and gradient of the pattern applied to the catheter tubing can vary. The UV blocking pattern can be applied in a mesh structure. The mesh structure can be formed according to the blocking pattern % curve shown in FIG. 9, which shows the blocking pattern % of the UVC energy over the length of the tubing and starts with about a 98% blocking pattern. The pattern may be a half tone or a pre design mesh of perforated material representing the pattern described. The pattern can be stepped from the 98% blocking to 0% blocking over the distance shown representing the required dose over that same distance. The mesh density of the UV blocking pattern can be selected and designed such that UV-C intensity reflected back into the catheter produces as a homogenous dosage along the length of the tubing as shown in FIG. 9. TiO2 can be added to a material or PTFE can be used, for example, as a viable UVC reflector. Alternatively, instead of being directly printed on the catheter shaft 3, the UV blocking pattern 10 can be provided on a separate substrate and adhesively joined to the catheter tubing 3.

Referring to FIG. 9, the depicted graph illustrates the dosing over different lengths of catheters. The distances in the graph refer to the distance from the edge of the installed disinfection device closest to the proximal end of the catheter to the tip of the proximal end of the catheter. The graph shows the inverse squared law losses and the required blocking percentages or exposure screen for homogenized dose delivery. The limits per 8 hours are based on the NIOSH or ISO standards for UV-C exposure.

The catheter 100 may include an RFID tag 40 that stores information associated with the catheter in memory. The RFID tag 40 can be interrogated by an RFID reader in the disinfection device to communicate catheter-specific information from the catheter 100 to the disinfection device 102. For example, the RFID tag can include information regarding the size, shape, or length of the catheter. The disinfection device can utilize this information to determine disinfection device settings, such as the appropriate UV-C intensity to disinfect the catheter. Alternatively, the RFID may include information stored in memory about the appropriate UV-C intensity value for that catheter 100, which can be used by the disinfection device to control the UV-C intensity.

The disinfection device or monitor can read the catheter RFID and understand the length of the catheter and adjust the characteristics of the disinfection device based on predetermined intensity requirements as well as safety testing. The disinfection device controller can programs the intensity into the lamp driver and can ensure that the UV dosage delivered is under the ISO standard for an 8 hour period. The disinfection device can start an 8 hour timer using a real time clock. After eight hours pass, another dose under the allowable level can be administered. The dosage delivered during the first eight hour period may not be sufficient to kill a target pathogen, but the cumulative low dosage provided over a sixteen to twenty-four hour period 16 to 24 hour period can be sufficient to start the disinfection process while simultaneously being safe for skin contact.

Figure 5B:
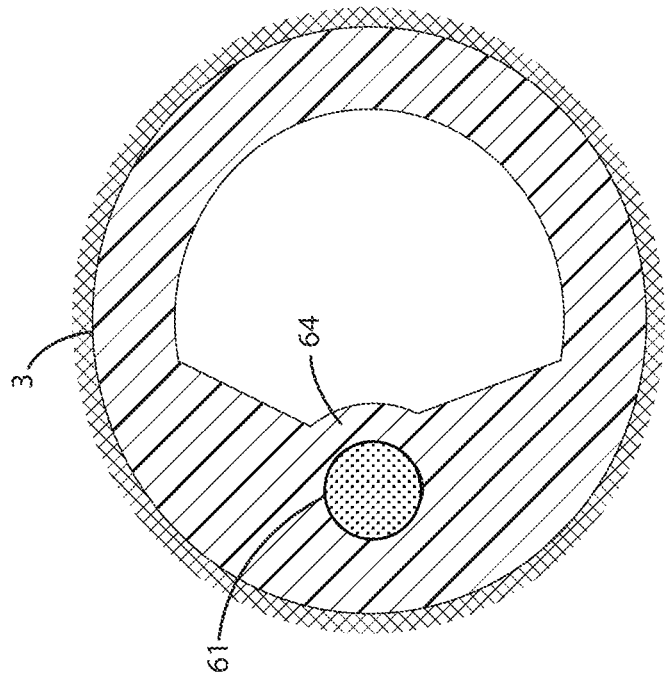
FIGS. 5A and 5B illustrate two different embodiments of UV-C distribution systems of the present invention.
Figure 5A:
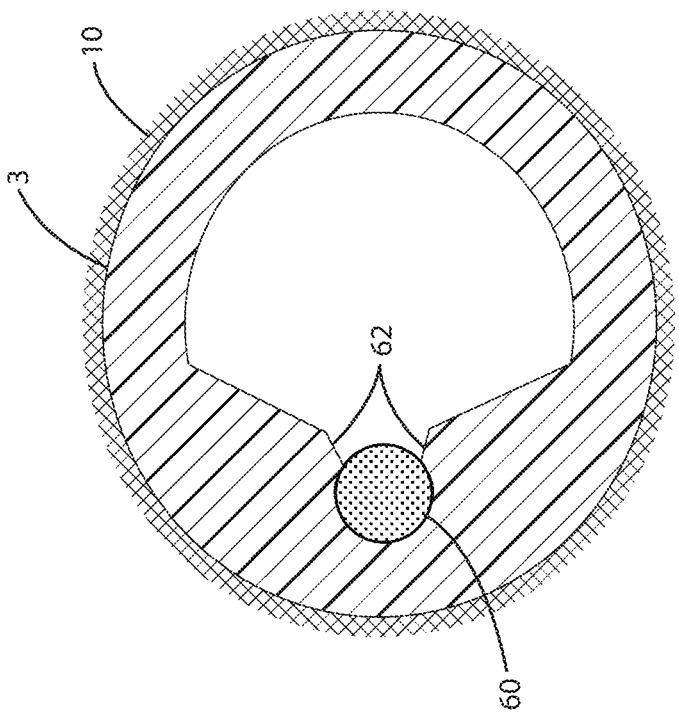

The catheter 100 may be outfit with a light tube system that includes one or more light guides 60 and/or light pipes 61. FIGS. 5A and 5B depict extruded catheter tubing with light tube systems that provide enhanced optical properties using quart fiber or other light tube systems. The catheter tube 3 can include a channel 62 with UV transmissive material 62 creating a friction fit for the light tube, as depicted in FIG. 5A. Alternatively, the catheter tube 3 may include a passage-way formed by UV transmissive material 64 internally through which the light tube can be routed, as depicted in FIG. 5B. The holding structure for the light tube systems may be formed by during extrusion or injection molding of the catheter tubing. Although the depicted embodiments each include a single light tube that runs the length of the catheter tubing, in alternative embodiments additional light tubes could be run along the catheter tubing 3. Further, in the depicted embodiments, the light tubes are held in place by the particular construction of the catheter tubing. In alternative embodiments, the light tube system could be fastened to the internal surface of the catheter tubing by other means, such as adhesive.

Referring to FIG. 5A, one embodiment of a catheter with a light guide 60 is depicted. The light guide 60 can be configured to receive light from the disinfection device and disperse it along its length. Specifically, the light guide 60 can assist in providing UV light from the UV source evenly and efficiently over the length of the UV transmissive tubing 3 of the catheter 100. The light guide can be a quartz fiber or other fiber cable that can utilize nanoparticles to extract light out the side of the fiber to enhance the lighted distance and losses for longer tubing. Further, the configuration and composition of the UV blocking pattern 10 can be selected in view of the characteristics of the light guide. That is, the UV intensity fall-off will be more subtle due to the light guide. For example, as depicted in FIG. 9, the drop off in intensity from 60 microwatts to the about 3 microwatts is more gradual.

In another embodiment, the light tube system includes one or more light pipes 61 positioned along the UV transmissive tubing 3 of the catheter 100. Instead of enhancing the lighted distance and losses, the light pipe can provide a reflective surface that results in delivering a rejuvenated UV source toward the proximal end of the body contact device. A UV reflecting, absorbing, or blocking pattern can be provided at the light pipe termination point to mask higher intensity UV light near the light pipe termination point and effectively reflect that energy back into the body contact device. Through the use of multiple light pipes and repeating UV blocking patterns, light pipes can be utilized to provide efficient and consistent UV dosage along the length of longer catheter tubing. Referring to FIG. 3, instead of the UV blocking zones 22, 24 representing different sections of gradients of one UV blocking pattern that stretches the length of the catheter, each section can represent a separate UV blocking pattern that corresponds to the UV intensity of a light pipe that terminates where the blocking pattern begins. The blocking patterns may be different from each other and from the blocking pattern 20 because although the light pipe can provide a rejuvenated UV source at a distance from the disinfection device, there will be some losses associated with the light pipe. The UV blocking pattern can be selected to provide a uniform or homogenous dosage based on the calculated or experimental UV intensities over the length of UV light delivered by each light pipe.

Figure 4:
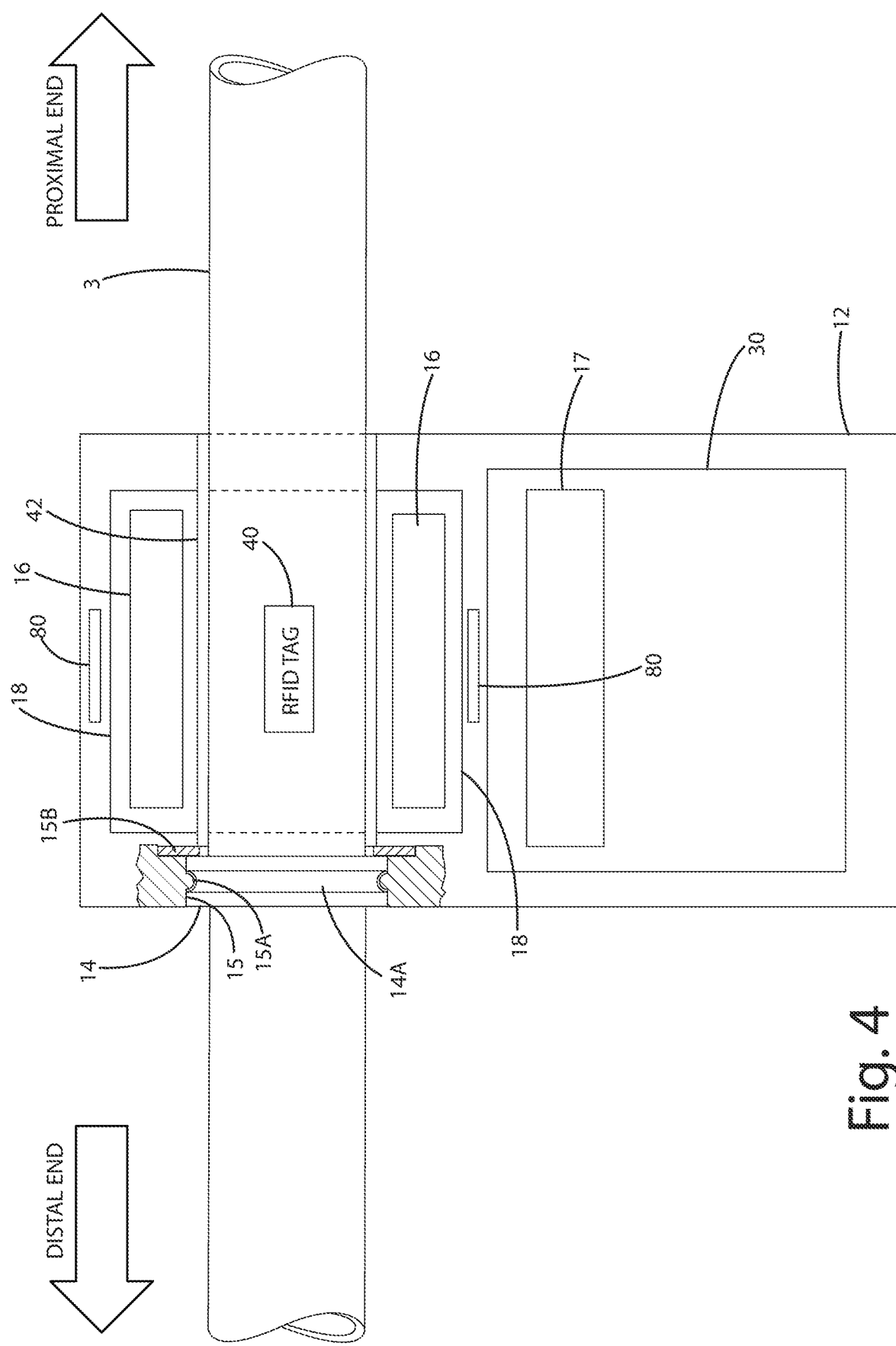
FIG. 4 illustrates a plan view of one embodiment of a UV-C attachment device of the present invention.

The disinfection device 102 will now be described in more detail. Perhaps as best seen in FIG. 4, the disinfection device 102 generally includes a housing 12, a reflector 18, a disinfection circuit 30, an RFID reader (not shown separate from the disinfection circuit in FIG. 4) and RFID coil 80, a UV power source or ballast 17, and a UV lamp 16. Fluid flows from the proximal end of the catheter to a storage device located at the distal end connected via the drainage port. The through mount snap detail and the RFID tag 40 for locating and identifying the intensity needed for that length of catheter are depicted in FIG. 4.

Figure 6:
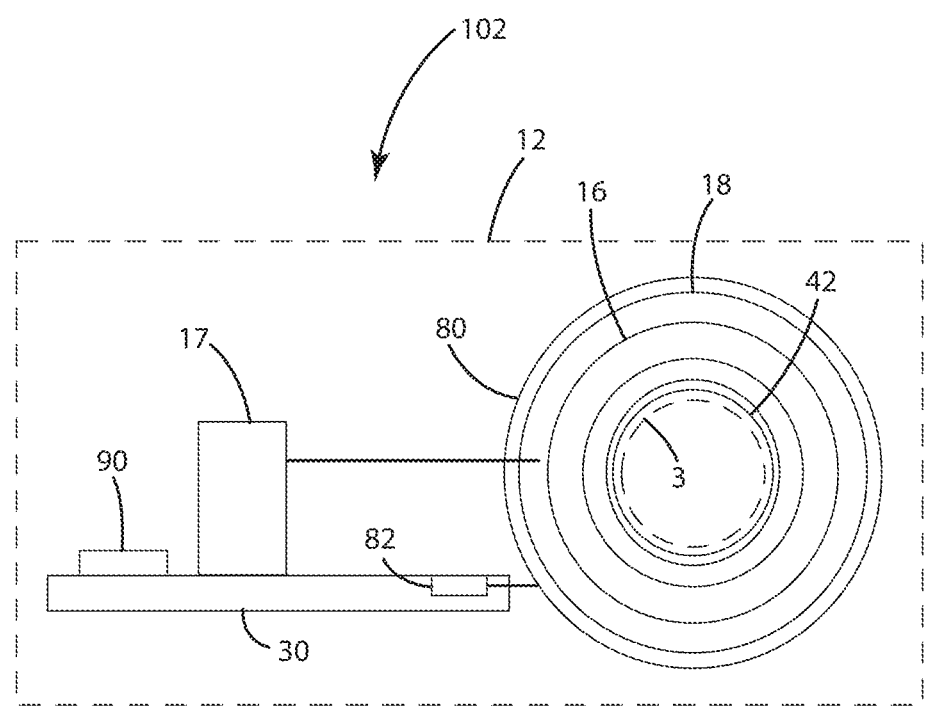
FIG. 6 illustrates a sectional plan view of one embodiment of a UV-C attachment device of the present invention.

The disinfection device 102 may include an integral attachment feature 14 for mounting the disinfection device to the catheter 100. The depicted embodiments of the disinfection device 102 include a passage-way 42 through which the catheter tubing 3 is routed. That is, the catheter can slip through the center or body of the disinfection device. The passage-way 42 can be made of a UV transmissive material. Alternatively, the passage-way 42 may be made of a UV opaque or semitransparent material and a portion of the passage-way 42 may include a UV transmissive window through which UV light can pass from the disinfection device to the catheter tubing 3. The UV lamp surrounds the passage-way 42 through which the catheter tube 3 passes. The disinfection device 102 may include a reflector 18 positioned radially outward from the UV lamp to direct UV-C radiation from the UV lamp 16 toward the proximal and/or distal end of the catheter. The UV-C radiation tends to be guided by the UV transmissive material of the catheter tubing along its length. Other light will tend to be reflected by the reflector 18 and eventually reflect back into the tubing 3 and eventually out of the disinfection device. The reflector 18 may be configured to urge the UV light toward the proximal end of the catheter tubing, but light may also be allowed to travel toward the distal end to provide disinfection along that surfaces as well. FIG. 6 illustrates a representative sectional view of the disinfection device 102, perhaps with a better view of the concentric arrangement of the RFID coil 80, UV reflector wall 18, UV lamp 16, passage-way 42, and tubing 3. That is, FIG. 6 shows the disinfection device cavity where the catheter passes through the disinfection device. The electronics 30 including battery 90, UV ballast 17, and RFID reader circuit 82 are located inside the sealed disinfection device housing 12.

The disinfection device itself can be made of UV transmissive material and the UV lamp can be configured to emit UV light toward the surface of the disinfection device to self-clean the disinfection device. The internal surface of the disinfection device housing can include a blocking pattern to limit exposure to appropriate levels for disinfecting the external surfaces of the disinfection device.

Figure 11:
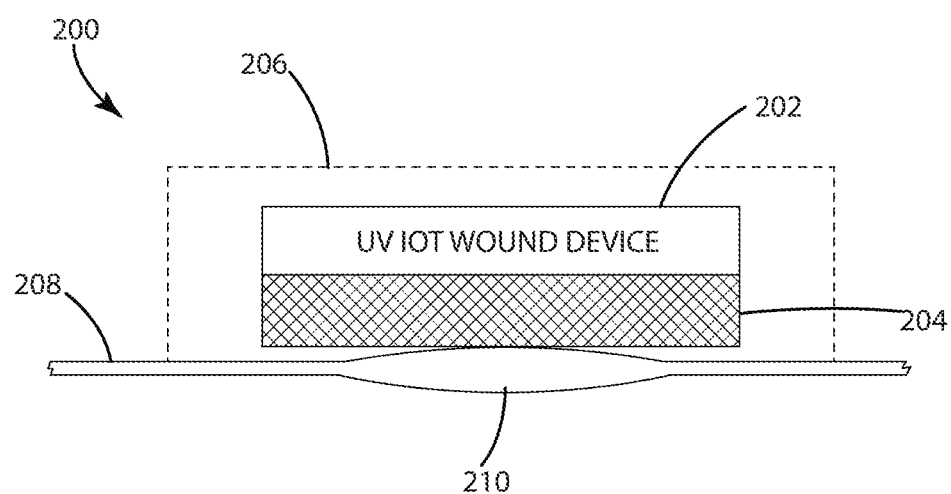
FIG. 11 shows another embodiment of a body contact device and UV disinfection device.

The disinfection device can be provided in a variety of different configurations for efficiently and effectively transmitting UV-C energy to the catheter. FIGS. 7A-B and 8A-B illustrate the inline and side profile versions of the through catheter disinfection device configurations. For example, one embodiment of the disinfection device, as depicted in FIGS. 7A-7B, attaches to the body contact device in an inline configuration. An alternative side profile configuration is depicted in FIGS. 8A-8B. In both embodiments, the UV lamp of the disinfection device surrounds the passage-way 42. In alternative embodiments, the disinfection device can be provided as a UV IOT wound device, as depicted in FIG. 11 configured to be secured along with a dressing 204 using an overwrap 206 to secure the UV IOT wound device to a user's skin 208.

The disinfection device can be programmed to disinfect the catheter periodically or based on a trigger. For example, in response to the fluid being sensed in the catheter, such as by measuring a thermal rise, or in response to local or remote user input. That is, the disinfection device can be activated by a user interface with a manual activation button or by way of a virtual user interface, for example a smart pone in communication with the disinfection device. Once activated, the disinfection device can initiate disinfection of the catheter through control of the UV source. The disinfection device can also monitor the disinfection process via the sensor system.

Figure 10:
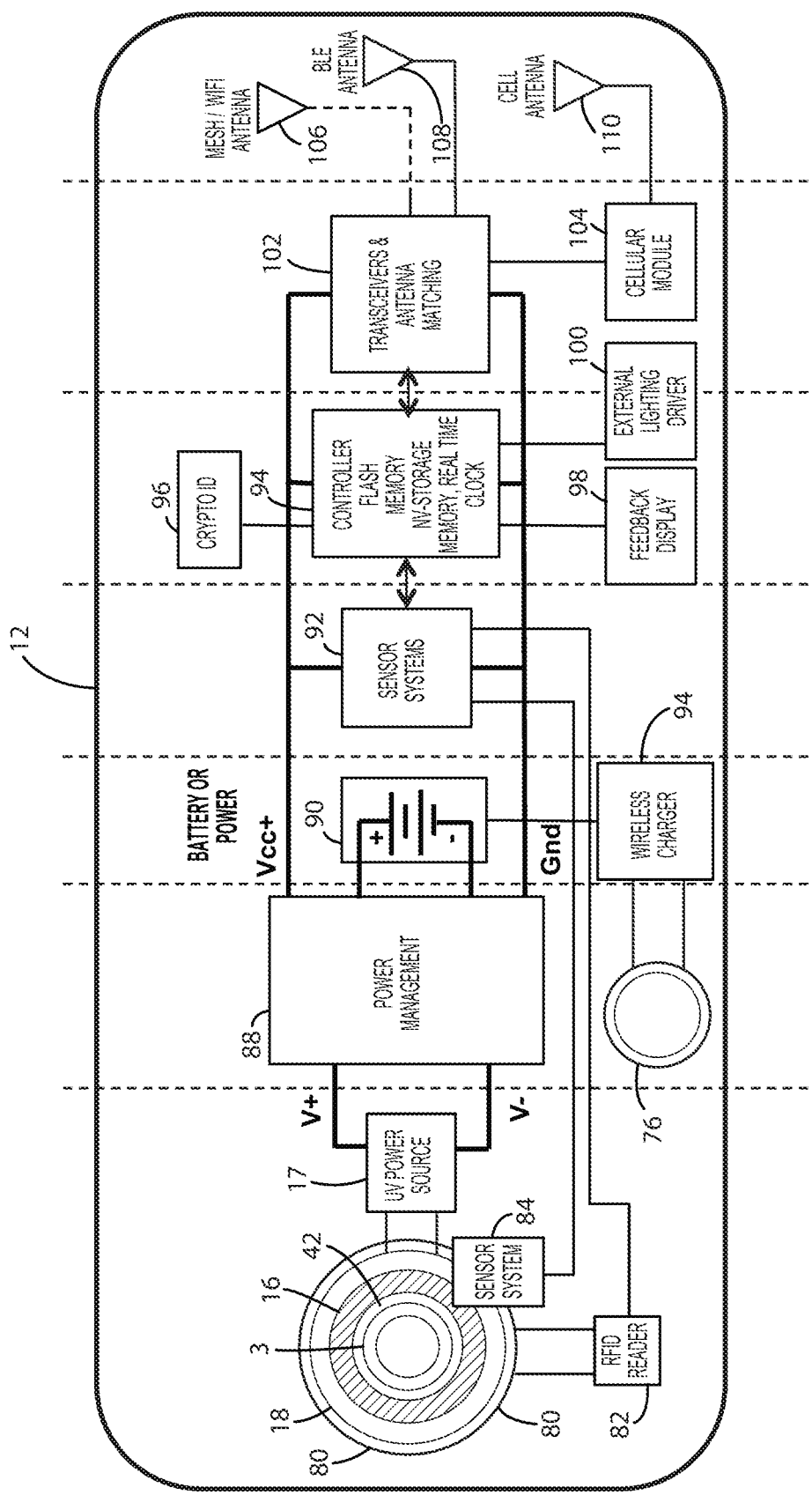
FIG. 10 shows one embodiment of a disinfection device including an electronics module.

The disinfection device 102 includes a control system, which will now be described in connection with the representative block diagram of FIG. 10. The control system can take the form of a sealed electronics package. The control system includes a disinfection device circuit that includes a controller 94 or processor that controls operation of the various components. The disinfection device circuit in the depicted embodiment includes a plurality of components installed on a printed circuit board assembly.

The disinfection device can include a battery and wireless charging to eliminate through physical input ports in the disinfection device. The system can include an RFID reader and coil 80 and a lamp driver for the UVC source. The RFID coil 80 can surround the passage-way 42 such that when the catheter 100 is installed in the disinfection device, the RFID tag 40 is in proximity to the RFID coil 80 and can be read by the RFID reader. As discussed above, the RFID reader can interface with an RFID tag 40 on the body contact device in order to determine the intensity needed to enable the proper overall intensity. The controller can accept sensor input in the form of acceleration, temperature, moisture, UVC intensity, and touch. The unit is Internet of Things capable and can utilize BTLE, cellular and WiFi for secure crypto communications and monitoring. The system can include an RGB LED display for communicating operation status and error codes. The control system may include non-volatile memory for tracking overall accumulators, drainage volume numbers, drainage per catheter, dosing and exposure, catheters used, types of catheters, dates used, durations and lamp hours and lamp starts, life data, and end of life counter for battery and lamp.

That is, in addition to communicating information about the catheter for use by the disinfection system, such as length and type of catheter, along with other characteristics, which can be utilized by the disinfection device to determine UV-C intensity and other operating parameters. The RFID system can also be utilized for end of life tracking. The RFID tag allows an authentication by the manufacturer that the body contact device is still good to be used in the field. It also assures can prevent a mismatch of catheter and electronics—for example by providing an error when the disinfection device is installed but the RFID tag does not match or cannot be read.

Referring to the communication circuitry, the disinfection device circuit can include communication circuitry 102, which can include one or more transceivers and antenna matching circuitry, such as a Mesh/Wifi antenna 106, a Bluetooth LE antenna 108, and/or a module 104 and accompanying cellular antenna 110. For example, the transceiver can be a WiFi, BTLE, BTLE Industrial, 400 or 900 Mhz transceiver. LTE or 5G+ modules make this cost effective and highly mobile. IoT solutions may not require setup and paring with these technologies in the future. BTLE can be used for monitoring devices within proximity to the disinfection device. The cellular module can be provided for advanced hub use. The antennas can all optionally be routed outside of the disinfection device housing 12. Alternatively, the antennas can be chip type antennas located on the printed circuit board assembly, or otherwise positioned within the housing 12 of the disinfection device.

The disinfection circuit can include a crypto ID circuit 96, a feedback display 98, and an external lighting driver 100. The control system may also include a physical or virtual user interface. The controller can also allow external communications and interface via the transceiver 102. The controller can also operate the feedback display and external lighting driver to provide user feedback.

The disinfection device circuit can include one or more sensors as part of a sensor system 84, 92 with one or more sensors that provide sensor output to the controller 94 or elsewhere within the disinfection device circuit. The sensor system 84, 92 can include a variety of different sensors. In the depicted embodiment, an RFID reader 82 is provided for receiving information about the catheter 100 from its associated RFID tag. In addition, other sensors, such as a capacitive, moisture, or temperature sensor can be provided. One or more of these sensors can be utilized to identify catheter use and frequency for dosing. The disinfection device and its sensor system can collect information from and/or about the body contact device. That data can be communicated to a third party database for entry into a patient's medical records. For example, the catheter type, time installed, usage and drainage volumes and times, or any other information sensed by the sensor system or RFID reader, can all be entered into a patient's medical record. The information can all be shared via crypto security.

The controller 94 can monitor temperature readings from on-board or external temperature sensor, which can be part of a sensor system 84, 92. For example, the disinfection device may include an ambient temperature sensor, a UV lamp temperature sensor, a microprocessor temperature sensor, and a passage-way temperature sensor for measuring the temperature of fluid passing through the tubing adjacent the passage-way 42. In UV IOT embodiments, such as that depicted in FIG. 11, additional, fewer, or different sensors may be included as part of the sensor system 84, 92. For example, the UV IOT device can include one or more different sensors configured to test for moisture or leakage from the dressing. Further, the UV IOT device can include sensors for detecting states and changes in states such as temperature, capacitance, and moisture sensors. The sensor system 84, 92 can also include one or more motion sensors, such as an accelerometer. In other embodiments, the controller 94 can also include an accelerometer that can measure acceleration of the device. The accelerometer can be utilized to track patient movement. For example, the controller can record raw acceleration data for analysis by a third party application, or the controller can be configured to determine patient movement in response to measuring a certain number of samples above a particular threshold value, which is indicative of patient movement. The controller can also include capacitive and voltage sensors, instead of or in addition to such sensors included elsewhere in the disinfection device sensor systems 84, 92. The touch sensors allow tracking if the patient is having an issue and can be programmed to trigger an alarm. The same touch sensor can be used for setup and configuration of the UI/UX. The voltage sensors can be used to assure proper battery voltage and wireless charging status. The sensors can assist with power management for the proper operation and maintenance of the device.

The disinfection device can provide thermal monitoring for drainage metering. In some embodiments, catheter tubing is inserted and routed through a passage-way in the disinfection device. The disinfection device includes a temperature sensor as part of the sensor system 84 that can sense temperature changes over time of fluid traveling through the catheter tubing 3. For UV IOT device embodiments, the disinfection device may include a temperature sensor that can sense changes over time of a fluid absorbent material adjacent the UV IOT device. The disinfection device can log times and temperatures related to flow and volume at specific times. The disinfection device can include an alert system. Utilizing the sensor output, the disinfection device can be configured to alert when a collection device is close to being filled, when there is leakage, or when there is essentially any other status change trackable by the sensor system 84, 92.

The disinfection device may include a battery or other power source 90 sized for dose and interval, of typical use. That is, the battery can be sized to provide sufficient power to operate the disinfection device for the typical duration of the use of one or a certain number of catheter devices.

The disinfection device may also include a wireless charging system 94 that includes a wireless power receiver 96, such as an inductive coil, that can receive wireless power from a wireless power charger. By providing wireless charging of the battery, the housing 12 can be provided as a waterproof protective enclosure.

The disinfection circuit may include a power management system 88. The power management system or power supply produces a regulated power source when voltage from the battery is present.

The UV source with ballast or power source with power and UV-C feedback. The UV-C lamp can be a cold cathode, low pressure Hg or one or more UV-C LEDs. The lamp reactor can surround catheter tubing 3, perhaps as best depicted in FIG. 4. Lamp energy can be directed toward the catheter, as discussed in detail above. The RFID reader 82 can read the RFID tag on the catheter to determine the type of catheter and/or appropriate UV disinfection intensity information. Temperature sensors can provide output indicative of the use and frequency of the catheter, which can also be utilized by the control system to adjust the UV-C intensity and timing. For a UV IOT device, the UV source can be configured differently. For example, the UV IOT device may include a window for directing UV light toward fluid absorbent material adjacent to the UV IOT device.

UV attachment device controller 94 can configure the UV lamp driver or UV power source 86 to provide a particular intensity that can deliver a dose under the ISO standard for an eight hour period. As discussed in more detail herein, a blocking pattern can be applied along the length of the body contact device can create a uniform dosage level along the length of the device despite the intensity fall off as the UV energy travels away from the source.

The controller 94 can monitor the dosage levels, for example, over an eight hour period or other time period, using a real time clock, for example onboard the controller. The controller is shown with a UVC sensor shown in FIG. 10 item 84 and this can be tracked very effectively with a real time clock and the UVC sensor over time. This data can be accumulated in a non-volatile accumulator and reported over time by patient. In this way, the UV attachment device can monitor and track compliance with any UV dosage requirements or safety standards to ensure compliance. By basing the intensity settings on the length of the body contact device and utilizing the blocking pattern, a consistent UV-C dosage can be provided that is within the safety standards, for example the National Institute for Occupational Safety and Health indicates that NIOSH safety limit for an eight hour period is intensity settings.

Table 1, below, provides the ISO15858 standards for dosage over time within an 8 hour period. Specifically, Table 1 lists the maximum permissible UV-C exposure times for radiation at 254 nm from ISO15858 in 2016. UV dose can be calculated by the product of UV light intensity and time. According to the chart, within an eight hour time period, a 3.3 microwatt dosage can be provided for 30 minutes out of the eight hour period in order to maintain less than a 6000 microwatt exposure within an eight hour time period.

Maximum Permissible UV-C Exposure Times for Radiation at 254 nm (From 15015858, 2016)

TABLE 1

| Dose | Time | Max Dose | Seconds |
| --- | --- | --- | --- |
| 3.3 uW | 30 min | 6000 | 1800 |
| 100 uW | 1 min | 6000 | 60 |
| 200 uW | 20 sec | 6000 | 30 |
| 1200 uW | 5 sec | 6000 | 5 |

Table 2, below, shows progressive dosing over time under permitted safety levels. In order to maintain dosage levels under the permissible exposure times, the control system controls the intensity and on time of the UV lamp within each eight hour period. However, the dosage provided within the initial eight hour period (or set of eight hour periods) may not be sufficient to kill target pathogens, but over time, for example several days, the cumulative dose is sufficient to continuously destroy the required surrogate while using time and minimal dosages to meet this goal. This allows safe contact while being lethal to the pathogens that can cause infections from the body contact devices.

Progressive Dosing Over Time Under Permitted Safety Levels

TABLE 2

|  | 8 Hours | 8 hours | 8 hours | 8 hours | 8 hours | 8 hours |
| --- | --- | --- | --- | --- | --- | --- |
| Intensity (uW) | 2.97 | 2.97 | 2.97 | 2.97 | 2.97 | 2.97 |
| On Time (Seconds) | 1,400 | 1,400 | 1,400 | 1,400 | 1,200 | 1,200 |
| Dose | 4,158 | 4,158 | 4,158 | 4,158 | 3,564 | 3,564 |
| Safety Allowance (per 8 hous) | 6,000 | 12,000 | 24,000 | 48,000 | 96,000 | 192,000 |
| Cumlative dose | 4,158 | 8,316 | 12,474 | 16,632 | 20,196 | 23,760 |
| Difference | 1,842 | 3,684 | 11,526 | 31,368 | 75,804 | 168,240 |
| Safety Margin | 30.70% | 30.70% | 48.03% | 65.35% | 78.96% | 87.63% |

Some embodiments can adjust progressive dosing based on certain factors. Progressive UV dosage results in a cumulative UV dosage over time. The effectiveness of that cumulative UV dosage can depend on a variety of factors. The disinfection device can monitor for a progressive trigger and reset the UV progressive dosing accordingly. For example, based on a model or test results a minimal progressive dosage required to achieve infection free body contact devices can be determined. The UV disinfection device can be configured to maintain that minimal progressive dosage through intermittent low UV dosing and monitoring the cumulative UV dosage provided. In response to the disinfection device sensor system detecting fluids passing through the catheter, or another progressive trigger, the cumulative UV dosage can be reset or adjusted and the UV disinfection device can control the progressive UV dosing accordingly to reach a UV cumulative dosing target.

Embodiments of the present invention can provide the following features:

- Dosing over time but under the NIOSH standard. Cumulative dosing while maintaining NIOSH provisions.
- Catheter mounting through the disinfecting device with snap detail for proper locating and reuse.
- Combination of UV-C and transmissive catheter materials for better dosage distribution
- UV IOT device with thermal monitoring and product life & use tracking.
- UVC Homogenization pattern to reduce and even out dosage over distance and track Inverse Squared Law calculations to even out the output for exposure over the distance.
- RFID identification of proper catheter and catheter mfg. details for tracking use and times of use.

U.S. Appl. No. 62/924,324, entitled "OPTICAL PROPERTIES AND METHODS FOR UV TREATMENT," to Baarman, was filed Oct. 22, 2019 and is hereby incorporated by reference in its entirety. This reference includes disclosures relating to methods and techniques for enhancing and modifying UV light patterns generated by UV disinfection devices to provide a desired UV light pattern, such as a generally uniform UV light pattern. The techniques detailed and described in the subject reference can be applied to the various embodiments of the body contact devices described herein. For example, the various methods and techniques for modifying UV light patterns can supplement or replace the UV blocking pattern discussed herein. Other references, which disclose various facets of UV disinfection devices are described in the following references: U.S. Pat. No. 9,242,018 to Cole et al., which is entitled "PORTABLE LIGHT FASTENING ASSEMBLY" and issued on Jan. 26, 2016; U.S. Pat. No. 9,974,873 to Cole et al., which is entitled "UV GERMICIDAL SYSTEM, METHOD, AND DEVICE THEREOF" and issued on May 22, 2018; International application No. PCT/US2019/023842 to Baarman et al., which is entitled "DISINFECTION BEHAVIOR TRACKING AND RANKING" was filed on Jun. 10, 2019; and International application No. PCT/US2019/036298 to Baarman et al., which is entitled "MOBILE DEVICE DISINFECTION" was filed on Jun. 10, 2019, which are all incorporated herein by reference in their entireties.

FIG. 11 shows a body contact device in the form of a wound/dressing device for covering or dressing a patient's wound or another medical device that is secured against an area of a patient's body surface susceptible to infection. The depicted body contact device includes a UV transmissive fluid absorbent material 204 along with an overwrap 206 for securing the UV transmissive fluid absorbent material 204 to a wound area 210 of a body surface 208. The disinfection device 200 may be a UV Internet of Things ("IOT") wound device 202. An overwrap 206 for securing the UV transmissive fluid absorbent material 204 can be utilized to secure the UV IOT wound device 202 to the fluid absorbent material 204 and also can be utilized to secure the combination to a wound area 210 of a body surface 208. The UV IOT wound disinfection device outputs a UV light pattern toward the UV transmissive fluid absorbent material for disinfecting the body contact device. The UV IOT device can have the same general functionality of the disinfection device described in connection with the catheter embodiment, depicted in FIG. 10. For example, the UV IOT device can include a sensor system with one or more sensors that can sense various characteristics relating to the body contact device, such as a moisture sensor for sensing a moisture level of the fluid absorbent material and any associated leakages and a temperature sensor for sensing a temperature of the fluid absorbent material 204. The UV IOT device 208 can also disinfect and track various states of the body contact device 200 such as those related to dressing conditions, movement, temperature, capacitance, moisture, and any other states or state changes associated with the body contact device.

The fluid absorbent material can be a dressing such as a sterile pad or compress. For example, the UV fluid absorbent material can be applicable to a wound to promote heating and protect the wound from further harm. The UV fluid absorbent material may be utilized in connection with IV catheters, ports, IV's, incisions, or essentially any other area of a patient's body capable of spreading or causing infection. The fluid absorbent material can be made from materials that are UV transmissive that allow UV light from the UV IOT device to pass through and disinfect at least the surfaces that contact the patient's body. The fluid absorbent material may be constructed from UV transmissive fibers woven into the fluid absorbent material. UV transmissive materials, such as PFA, FEP, and PTFE, can be utilized with common textile materials to create enhanced fibers or filaments with these UV transmissive materials, which provide enhanced UV distribution in the fluid absorbent material. Using a percentage of these fibers within a typical dressing or fluid absorbent material helps distribute UV light throughout the material and reach the proximal surface to better treat any biological activity trapped within the material as well as the surface. For example, a UV transmissive fiber or filament can be mixed with other materials like cotton to create a fabric with increased UV transmissive characteristics that enhance disinfection of the product when subjected to UVC light. The enhanced fibers can be made in various sizes for flexibility, diffusal, and wear characteristics.

The overwrap 206 can be an adhesive tape or bandage that secures the dressing or fluid absorbent material to the body surface. The overwrap 206 may itself be a UV transmissive material and the UV IOT device may direct UV light toward the overwrap to disinfect the external surface. Alternatively, the overwrap 206 may be UV reflective or absorbent material or have an internal surface coated with a UV reflective or absorbent coating in order to reflect or absorb UV light that reaches the internal surface of the overwrap 206 from the UV IOT device.

The body contact device 200 of FIG. 11 includes a UV transmissive fluid absorbent material 204, a disinfection device 202 for disinfecting said fluid absorbent material 204. The disinfection device 202 including a housing, a UV source disposed within said housing, and a controller configured to control the UV source, as discussed in connection with FIG. 10. The body contact device also includes an overwrap 206 for securing the fluid absorbent material and the disinfection device to a surface 208. The controller can be configured to control the intensity and on-time of the UV source to provide a UV light with less than 6000 microwatts of energy per eight hour period. The UV transmissiveness of the fluid absorbent material can be selected by varying the amount of UV transmissive fibers, being coated with a UV transmissive coating, varying the thickness of the material, loading the material with additives that have UV light altering properties, or essentially any other way of varying the UV transmissiveness of the fluid absorbent material. The UV disinfection device can include a wide variety of different sensors including a temperature sensor configured to monitor the temperature of the fluid absorbent material, a moisture sensor configured to monitor the moisture level of the fluid absorbent material, a capacitive sensor to measure the capacitance associated with the UV absorbent material, or essentially any other sensor to provide sensor readings to the controller for tracking and monitoring operation of the disinfection device. The controller can be configured to track UV dosage applied to the UV transmissive fluid absorbent material and provide information to a remote device about the state or change in state of the disinfection operation, including any of the sensor readings.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The embodiments of the invention in which an exclusive property or privilege is claimed are defined as follows:

1. A disinfection device for disinfecting a body contact device, the disinfection device comprising:
   a housing for mounting said disinfection device to the body contact device;
   a UV source disposed within said housing;
   an RFID reader configured to interrogate an RFID tag associated with the body contact device;
   a controller configured to control an intensity of said UV source based on output from said RFID reader; and
   wherein said controller is configured to track UV dosage applied to the body contact device.

2. The disinfection device of claim 1 wherein said controller is configured to control the intensity and on-time of said UV source to less than 6000 microwatts per eight hour period.

3. The disinfection device of claim 1 wherein the housing includes a UV transmissive passage-way for routing the body contact device there-through, said UV source disposed radially about said UV transmissive passage-way, and wherein said disinfection device further includes a UV reflector disposed radially about said UV source to reflect UV energy.

4. The disinfection device of claim 1 wherein said output from said RFID reader includes UV disinfection information specific to the body contact device, wherein the UV disinfection information includes at least one of a UV intensity information and body contact device size information.

5. The disinfection device of claim 1 including a thermal sensing system for tracking drainage from the body contact device.

6. The disinfection device of claim 1 wherein said controller tracks cumulative dosage per eight hours and controls the UV source intensity and UV source on-times based on the cumulative dosage.

7. The disinfection device of claim 1 wherein said controller tracks the UV source life.

8. A body contact device comprising:
   an RFID tag;
   a UV transmissive tube having a distal end and a proximal end;
   an integral attachment feature positioned toward said distal end of said UV transmissive tube, said integral attachment feature configured to removably attach a disinfection device;
   a UV blocking pattern disposed adjacent to said UV transmissive tube.

9. The body contact device of claim 8 wherein said UV blocking pattern includes a gradient.

10. The body contact device of claim 8 wherein said UV blocking pattern includes titanium dioxide and is printed on said UV transmissive tube.

11. The body contact device of claim 8 wherein said RFID tag includes at least one of UV intensity information and body contact device length information.

12. The body contact device of claim 8 including a light guide positioned along the internal surface of the UV transmissive tubing that assists in providing UV light evenly and efficiently to the proximal end of the UV transmissive tubing.

13. The body contact device of claim 8 including a light pipe positioned along the internal surface of the UV transmissive tubing having a termination point between the integral attachment feature and the proximal end of the UV transmissive tube, wherein the termination point of the light pipe provides a rejuvenated UV source, wherein the body contact device further includes an additional UV blocking pattern adjacent said UV transmissive tube proximate said light pipe termination point to mask UV light exiting said light pipe termination point toward said proximal end of the UV transmissive tubing.

14. A disinfection system comprising:
a body contact device including:
- an RFID tag;
- a UV transmissive tube having a distal end and a proximal end;
- an integral attachment feature positioned toward said distal end of said UV transmissive tube, said integral attachment feature configured to removably attach a disinfection device; and
- a UV blocking pattern disposed adjacent to said UV transmissive tube;

a disinfection device for disinfecting said body contact device, the disinfection device including:
- a housing for mounting said disinfection device to the body contact device;
- a UV source disposed within said housing;
- an RFID reader configured to interrogate an RFID tag associated with the body contact device; and
- a controller configured to control an intensity of said UV source based on output from said RFID.

15. The disinfection system of claim 14 wherein said controller is configured to control the intensity and on-time of said UV source to less than 6000 microwatts per eight hour period.

16. The disinfection system of claim 14 wherein the housing includes a UV transmissive passage-way for routing the body contact device there-through, said UV source disposed radially about said UV transmissive passage-way, and wherein said disinfection device further includes a UV reflector disposed radially about said UV source to reflect UV energy.

17. The disinfection system of claim 14 wherein said output from said RFID reader includes UV disinfection information specific to the body contact device, wherein the UV disinfection information includes at least one of a UV intensity information and body contact device size information.

18. The disinfection system of claim 14 wherein said controller is configured to track UV dosage applied to the body contact device.

19. The disinfection system of claim 14 including a thermal sensing system for tracking drainage from the body contact device.

20. The disinfection system of claim 14 wherein said controller tracks cumulative dosage per eight hours and controls the UV source intensity and UV source on-times based on the cumulative dosage.

21. The disinfection system of claim 14 wherein said controller tracks the UV source end of life.

22. The disinfection system of claim 14 wherein said UV blocking pattern includes a gradient.

23. The disinfection system of claim 14 wherein said UV blocking pattern includes titanium dioxide and is printed on said UV transmissive tube.

24. The disinfection system of claim 14 wherein said RFID tag includes at least one of UV intensity information and body contact device length information.

25. The disinfection system of claim 14 including a light guide positioned along the internal surface of the UV transmissive tubing that assists in providing UV light evenly and efficiently to the proximal end of the UV transmissive tubing.

26. The disinfection system of claim 14 including a light pipe positioned along the internal surface of the UV transmissive tubing having a termination point between the integral attachment feature and the proximal end of the UV transmissive tube, wherein the termination point of the light pipe provides a rejuvenated UV source, wherein the body contact device further includes an additional UV blocking pattern adjacent said UV transmissive tube proximate said light pipe termination point to mask UV light exiting said light pipe termination point toward said proximal end of the UV transmissive tubing.

* * * * *